United States Patent
Lukacs

(10) Patent No.: US 8,197,866 B1
(45) Date of Patent: Jun. 12, 2012

(54) HERBAL TREATMENT FOR DIABETES MELLITUS, TYPE II

(76) Inventor: Maria Lukacs, St. Petersburg, FL (US)

( * ) Notice: Subject to any disclaimer, the term of this patent is extended or adjusted under 35 U.S.C. 154(b) by 414 days.

(21) Appl. No.: 12/383,074

(22) Filed: Mar. 19, 2009

(51) Int. Cl.
*A61K 36/61* (2006.01)
*A61K 36/14* (2006.01)
*A61K 36/53* (2006.01)
*A61K 36/752* (2006.01)
*A61K 36/45* (2006.01)
*A61K 36/63* (2006.01)
*A61K 36/734* (2006.01)

(52) U.S. Cl. .......... 424/728; 424/742; 424/74; 424/736; 424/732; 424/765

(58) Field of Classification Search .................. None
See application file for complete search history.

(56) References Cited

U.S. PATENT DOCUMENTS

| 6,303,586 B1 * | 10/2001 | McPeak et al. ............ 514/54 |
| 6,576,270 B2 | 6/2003 | Leko |
| 2006/0110471 A1 * | 5/2006 | Nichols .................... 424/745 |

OTHER PUBLICATIONS 2008 http://www.nytimes.com/2008/11/26/dining/263lrex.html.*
Reasner et al., Treatment of Type 2 Diabetes mellitus: A Rational Approach Based on Its Pathophysiology, 2001, Am Fam Physician, 63: 1687-1694.*

* cited by examiner

*Primary Examiner* — Patricia Leith
*Assistant Examiner* — Catheryne Chen
(74) *Attorney, Agent, or Firm* — Edward P Dutkiewicz

(57) ABSTRACT

A herbal treatment for Diabetes Mellitus, Type II comprises a first volume of herbal oils and a first weight of ground herbs. The mixture of the oil and ground herbs forms a paste, which is dispensed in a gel capsule.

4 Claims, No Drawings

HERBAL TREATMENT FOR DIABETES MELLITUS, TYPE II

BACKGROUND OF THE INVENTION

Rule 1.78(F)(1) Disclosure

The Applicant has not submitted a related pending or patented non-provisional application within two months of the filing date of this present application. The invention is made by a single inventor, so there are no other inventors to be disclosed. This application is not under assignment to any other person or entity at this time.

FIELD OF THE INVENTION

The present invention relates to a herbal treatment for Diabetes Mellitus, Type II and more particularly pertains to a way of integrating herbal components into a treatment for Diabetes Mellitus, Type II.

DESCRIPTION OF THE PRIOR ART

The use of herbal therapy is known in the prior art. More specifically, herbal therapy previously devised and utilized for the purpose of preventing and treating physical conditions are known to consist basically of familiar, expected, and obvious components, notwithstanding the myriad of formulations encompassed by the crowded prior art which has been developed for the fulfillment of countless objectives and requirements.

While the prior art devices fulfill their respective, particular objectives and requirements, the aforementioned patents do not describe an herbal treatment for Diabetes Mellitus, Type II that allows the user to apply an herbal therapy as part of a treatment for Diabetes Mellitus, Type II.

In this respect, the herbal treatment for Diabetes Mellitus, Type II according to the present invention substantially departs from the conventional concepts and formulations of the prior art, and in doing so provides a formulation primarily developed for the purpose of providing the user with a way of integrating herbal components into a treatment for Diabetes Mellitus, Type II.

Therefore, it can be appreciated that there exists a continuing need for a new and improved herbal treatment for Diabetes Mellitus, Type II which can be used for integrating herbal components into a treatment for Diabetes Mellitus, Type II. In this regard, the present invention substantially fulfills this need.

SUMMARY OF THE INVENTION

In view of the foregoing disadvantages and shortcomings inherent in the known types of herbal therapy now present in the prior art, the present invention provides an improved herbal treatment for Diabetes Mellitus, Type II. As such, the general purpose of the present invention, which will be described subsequently in greater detail, is to provide a new and improved herbal treatment for Diabetes Mellitus, Type II which has all the advantages of the prior art and none of the disadvantages.

To attain this, the present invention essentially comprises an herbal treatment for Diabetes Mellitus, Type II mixture comprising several components, in combination. The herbal treatment for Diabetes Mellitus, Type II is made up of a mixture of oils and herbs. In the preferred embodiment the dispensing modality for the mixture is in the form of a capsule. In other embodiments, the mixture for the treatment of Diabetes Mellitus, Type II may be in the form of an additive, which may be added to a liquid to be consumed as a drink.

Like medications, specific herbs have specific pharmacologic properties. Herbal oils are mixed with ground herbs so as to form the mixture herein described.

There has thus been outlined, rather broadly, the more important features of the invention in order that the detailed description thereof that follows may be better understood and in order that the present contribution to the art may be better appreciated. There are, of course, additional features and/or formulations of the invention that will be described hereinafter and which will form the subject matter of the claims attached.

In this respect, before explaining at least one embodiment of the invention in detail, it is to be understood that the invention is not limited in its application to the details of the formulation of, and the arrangements of, the components set forth in the following description. The invention is capable of other embodiments and of being practiced and carried out in various ways. Also, it is to be understood that the phraseology and terminology employed herein are for the purpose of descriptions and should not be regarded as limiting.

As such, those skilled in the art will appreciate that the conception, upon which this disclosure is based, may readily be utilized as a basis for the other formulations, methods and systems for carrying out the several purposes of the present invention. It is important, therefore, that the claims be regarded as including such equivalent constructions insofar as they do not depart from the spirit and scope of the present invention.

It is therefore an object of the present invention to provide a new and improved herbal treatment for Diabetes Mellitus, Type II which has all of the advantages of the prior art herbal therapy and none of the disadvantages.

It is another object of the present invention to provide a new and improved herbal treatment for Diabetes Mellitus, Type II which may be easily and efficiently manufactured and marketed.

An even further object of the present invention is to provide a new and improved herbal treatment for Diabetes Mellitus, Type II which is susceptible of a low cost of manufacture with regard to both materials and labor, and which accordingly is then susceptible of low prices of sale to the consuming public, thereby making such herbal treatment for Diabetes Mellitus, Type II economically available to the buying public.

Even still another object of the present invention is to provide a herbal treatment for Diabetes Mellitus, Type II for wa way of integrating herbal components into a treatment for Diabetes Mellitus, Type II.

Lastly, it is an object of the present invention to provide a new and improved herbal treatment for Diabetes Mellitus, Type II mixture comprising, in combination, a combination of oils being mixed with a combination of herbs for the treatment of Diabetes Mellitus, Type II, provided in a gel capsule.

These together with other objects of the invention, along with the various features of novelty which characterize the invention, are pointed out with particularity in the claims annexed to and forming a part of this disclosure. For a better understanding of the invention, its advantages and the specific objects attained by its uses, reference should be had to the accompanying descriptive matter concerning the preferred embodiments of the invention.

DESCRIPTION OF THE PREFERRED EMBODIMENT

The preferred embodiment of the new and improved herbal treatment for Diabetes Mellitus, Type II embodying the principles and concepts of the present invention will be described.

The present invention, the herbal treatment for Diabetes Mellitus, Type II is comprised of a plurality of components. Such components in their broadest context include an herbal oil mixture and a ground herbal mixture for the treatment of Diabetes Mellitus, Type II. Such components are combined so as to attain the desired objective.

The herbal oils are obtained by any one of a number of well known methods of extraction of oils from plants. The method used to extract the herbal oil does not affect the formulation, and is not determinative of the effectiveness of the mixture. The oil, as it is extracted, is not further purified or treated, but once the oil is separated from the extraction method, the oil is ready for use in this herein described formulation. As such methods of oil extraction are well known in the art, there will be no further discussion of such methods.

The ground herbs are obtained by the grinding of each of the ingredients so as to render a fine powder of the herb, with the resultant ground herb having the powder consistency of flour. The method used to grind the herbs does not affect the formulation, and is not determinative of the effectiveness of the mixture. No further separation is required. As such methods of grinding are well known in the art, there will be no further discussion of such methods.

The herbal treatment for Diabetes Mellitus, Type II mixture comprises several components, in combination. The two major components are an herbal oil mixture component and a mixture of ground herbal components.

The components are:

(1) *Juniperum Communis*, a small evergreen shrub, never attaining the height of a tree, with many very close branches. The leaves are attached to the stem in threes. The fruit is fleshy, of dark-purplish color, ripening the second year from the flower. Juniper grows in dry woods and hills, and flowers in May. The oil is contained in the spirituous liquor called Holland gin. The berries yield their properties to hot water and alcohol. The berries and oil are stimulating, carminative, and diuretic.

(2) *Eucalyptus Globulus*, is a powerful antiseptic and destructive to low forms of life, a stimulating expectorant and an efficient diaphoretic. It is a remedy with marked effects on catarrhal processes, malaria, and intestinal disturbance. Eucalyptus Globulus is reported to be anodyne, antiperiodic, antiphlogistic, antiseptic, astringent, deodorant, diaphoretic, expectorant, febrifuge, hemostatic, inhalant, insect repellant, rubefacient, sedative yet stimulant, suppurative, and vermifuge. The bluegum eucalyptus is a folk remedy for abscess, arthritis, asthma, boils, bronchitis, burns, cancer, catarrh, cold, cough, croup, cystitia, diabetes, diptheria, dysentery, dyspepsia, fever, flu, grippe, inflammation, laryngitis, leprosy, malaria, miasma, phthisis, rhinitis, sores, sorethroat, spasms, tuberculosis, tumors, vaginitis, wounds, and worms. It has been argued that the daily drinking of a leaf infusion of Eucalyptus Globulus can reverse diabetes in 8 days. Eucalyptus Globulus leaves have been placed in the bath for the treatment of rheumatism. Homeopaths use the plant for bronchitis, colds, flu, laryngitis, and rheumatism. In Asia, the leaf oil, clearly poisonous in large quantities, is regarded as anesthetic, antibiotic, antiperiodic, expectorant, febrifuge, and vermifuge, and it is used for asthma, bronchitis, influenza, and tuberculosis. In Australia, the leaves of the bluegum are still widely used as a household remedy in the treatment of many diseases and minor complaints. In Britain and Europe the essential oil, which is powerfully antiseptic, was given for fevers and febrile conditions, for pulmonary tuberculosis, and was applied or inhaled for relieving asthma, bronchitis, sorethroat, croup, whooping-cough, scarlet fever, and even diptheria and typhoid. The dried leaves were also smoked like cigarettes for asthma while the oil in the form of an aperitif was taken as a digestive. Europeans in Africa and Africans themselves may wear the leaf in the hat or place it around the residence as a flu preventative. It is also regarded as a malaria preventative. African herbalists believe the root is purgative. The leaves of Eucalyptus Globulus contain 70-80% eucalyptol (cineol). Also includedare terpineol, sesquiterpene alcohols, aliphatic aldehydes, isoamyl alcohol, ethanol, and terpenes. Tannin is not so copious in the leaves as of many other Eucalyptus species. The kino, containing 28.7% kino-tannin and 47.9% catechin contains the very antibiotic citriodorol. Verma et al. (1978) found 20.2% a-pinene, 25.2% b-pinene, and only 16.8% cineole in the cv 'Mysore'. Fresh leaves contain caffeic and gallic acids, dry leaves, ferulic and gentisic, and quercetol, quercitrine, rutin, and a mixture of quercetol hyperoside and glaucoside. N-titriacontan-16, 18-dione was identified as the compound responsible for antioxidant activity in the leaf wax.

(3) *Rosmarinus Officinalis*: is commonly grown in the herb garden as a domestic remedy, used especially as a tonic and pick-me-up when feeling depressed, mentally tired, or nervous. Research has shown that the plant is rich in volatile oils, flavanoids and phenolic acids, which are strongly antiseptic and anti-inflammatory. Rosmarinic acid has potential in the treatment of toxic shock syndrome, whilst the flavonoid diosmin is reputedly more effective than rutin in reducing capillary fragility. Rosmarol, an extract from the leaves, has shown remarkably high antioxidant activity.

The whole plant is antiseptic, antispasmodic, aromatic, astringent, cardiac, carminative, cholagogue, diaphoretic, emmenagogue, nervine, stimulant, stomachic and tonic. An infusion of the flowering stems made in a closed container to prevent the steam from escaping is effective in treating headaches, colic, colds and nervous diseases. A distilled water from the flowers is used as an eyewash. The leaves can be harvested in the spring or summer and used fresh, they can also be dried for later use.

An essential oil is distilled from the stems and leaves and is often used medicinally. The oil distilled from the flowering tops is superior but not often available. The oil may applied externally as a rubefacient, added to liniments, rubbed into the temples to treat headaches and used internally as a stomachic and nervine.

The plant contains some tannic acid, together with a resin and a bitter principle and a volatile oil. The chief constituents of the oil are Borneol, bornyl acetate and other esters, a special camphor similar to that possessed by the myrtle, cineol, pinene and camphene. The oil is colorless, with the odor of Rosemary and a warm camphoraceous taste. The chief adulterants of oil of Rosemary are oil of turpentine and petroleum. Rosemary yields its virtues partly to water and entirely to rectified spirits of wine. The extraction of the oil of Rosmarinus Officinalis may be accomplished by steam distillation. The part of Plant used is the flowers. The aromatic qualities are: herbaceous, minty, woody. The extract is used to treat acne, arteriosclerosis, asthma, bronchitis, candida, cellulite, poor circulation, colds, colitis, dandruff, dermatitis, dysmenorrhea, dyspepsia, eczema, fatigue, flatulence, flu, fluid retention, gout, oily hair, promotion of hair growth, prevention of hair loss, headache, hypotension, infections, insect repellant, jaundice, lice, liver problems, low blood pressure, muscle pain, neuralgia, ovary problems, palpitations, rheumatism, scalp conditions requiring scalp stimulations, sinusitis, stress, tachycardia, testicular problems, varicose veins, and whooping cough.

(4) *Citrus Medical* Var. Limonum, or Lemon, is an oval or roundish fruit resembling the orange, and containing a pulp usually intensely acid. It is produced by a tropical tree of the genus {Citrus}, the common fruit known in commerce being that of the species {Citrus Limonum} or {Citrus Medica} (var. Limonum). There are many varieties of the fruit, some of which are sweet. The oil extracted from the lemon is a pale yellow, greenish-yellow liquid, characteristic odor and taste of the outer part of fresh lemon peel, having a sp. gr. of 0.853, dextrorotatory, soluble in alcohol, dehydrated alcohol, carbon disulphide, glacial acetic acid; neutral, slightly acid; contains at least four aldehydes. The oil extracted from the lemon is used as a stimulant, stomachic, added usually to infusions, tinctures, etc. The extract is use chiefly for flavoring. Citrus is well known to contain large amounts of vitamin C, and is used as a preventative for diseases caused by a lack of vitamin C. The citrus oil extract may be used daily as a preventive, for acute rheumatism; locally in sunburn, pruritus of scrotum, uterine hemorrhage after labor, or as a gargle in diphtheria.

(5) *Galega Officinalis Herba*: is a traditional medicinal plant from Bulgaria. It was found that the aqueous extract of *Herba Galegae* suppressed platelet aggregation in vitro induced by adenosine diphosphate, epinephrine, thrombin and collagen. The compounds with anti-aggregating action have not as yet been isolated from *Galega officinalis*.

*Galega officinalis* (galega, Goat's Rue, French Lilac) is well known for its hypoglycaemic action and has been used as part of a plant mixture in the treatment of diabetes mellitus. During pharmacological investigations of an ethanolic extract of a powdered mixture of equal proportions of *G. officinalis, Cressa cretica, Mangifera indica* and *Syzygium jambolanum*, a weight reducing effect of galega was discovered.

The novel weight reducing effect of galega in mice has been investigated. Galega herb (10% w/w in the diet) caused a significant reduction in body weight in both normal and genetically obese animals treated for 28 days when compared with respective controls ($P<0.01$). In normal mice, the weight loss was reversible and initially associated with a transient reduction in food intake but was then maintained even in the presence of increased eating above the control level. Pair-fed normal mice receiving galega for seven days also showed significant weight loss ($P<0.01$, compared with the control) in the presence of increasing food intake. In sharp contrast, weight loss in galega-treated genetically obese mice was accompanied by a persistent reduction in food intake over the 28-day treatment period. Post-mortem examinations of all galega-treated mice revealed a striking absence of body fat. Serum glucose was significantly reduced in both strains of mice receiving galega for 28 days ($P<0.01$), whereas serum insulin was significantly reduced only in obese mice ($P<0.01$). In summary, together with its established hypoglycaemic effects, galega has a novel weight reducing action that, in normal mice, is largely independent of a reduction in food intake. The mechanism of the weight reducing action of galega is unclear but involves loss of body fat.

(6) *Myrtilli Fructus* (bacca) Herba: also known as Bilberry, is a close relative of blueberry, and has a long history of medicinal use. The dried fruit has been popular for the symptomatic treatment of diarrhea, for topical relief of minor mucus membrane inflammation, and for a variety of eye disorders, including poor night vision, eyestrain, and myopia. Bilberry fruit and its extracts contain a number of biologically active components, including a class of compounds called anthocyanosides. These have been the focus of recent research in Europe. Bilberry extract has been evaluated for efficacy as an antioxidant, mucostimulant, hypoglycemic, anti-inflammatory, "vasoprotectant," and lipid-lowering agent. Although preclinical studies have been promising, human data are limited and largely of poor quality.

(7) *Carataegus Fructus Herba*: also known as the is hawthorn berry or flower produces an extract obtainable by any menthod in which water, alcohol, acetic acid, liqueur wine, a super-critical gas, a super-critical liquid or mixtures thereof, act as the extraction agent. According to another embodiment of the invention, the formulation is a pressed juice.

Flowers and leaves contain mixtures of chlorogenic acid and flavonoids such as quercin, hyperoside (quercetin 3-galactoside), vitexin and vitexin 4 rhamnoside. Chlorogenic acid and caffeic acid have some analgesic effects. Quercetin has multiple actions: antiarrhythmic, antihepatotoxic and inhibitor of cAMP-phosphodies. Other flavonoids identified in *Crataegus* species are luteolin, luteolin-3?7 diglucosides, apigenin, apegenin-7-O-glucoside and rutin. Luteolin is an effective smooth muscle relaxant and protects the heart lipids against doxorubicin-induced lipid peroxidation. In addition, luteolin 5-rutinoside has achieved a marked anti-diabetic activity in streptozocin-induced diabetes. Apigenin and luteolin inhibit tumor formation. Luteolin decreases aromatase enzyme activity; apigenin showed inhibitory effect on TPA-mediated tumor promotion and is antimutagenic.

(8) *Cynosbati Fructus Sine Semimibus* & Herba extract: also known as Rosehip (*Fructus cynosbati*) extract—is a source of a number of vitamins (A, K, B, E), however, primarily a source of a natural vitamin C. It promotes the regeneration of cartilages and protects them against toxic damage.

The oil mixture is comprised of the following;

| | |
|---|---|
| *Juniperum Communis*: | between about 20 drops and 40 drops, with the preferred amount being 30 drops; |
| *Eucalyptus Globulus* | between about 20 drops and 40 drops, with the preferred amount being 30 drops; |
| *Rosmarinus Officinalis* | between about 20 and 60 drops, with the preferred amount being 38 drops; |
| *Citrus Medical* Var. *Limonum* | between about 20 drops and 60 drops, with the preferred amount being 38 drops. |
| Total Drops in the preferred embodiment: | 136 drops. |

The ground herbal mixture is comprised of the following;

| | |
|---|---|
| *Galega Officinalis Herba* | between about 1 mgms and 10 mgs, with the preferred amount being 5 mgms; |
| *Myrtilli Fructus (bacca) Herba* | between about 2 mgms and 12 mgms, with the preferred amount being 7 mgms; |
| *Carataegus Fructus Herba* | between about 2 mgms and 10 mgms, with the preferred amount being 6 mgms; |
| *Cynosbati Fructus Sine Semimibus* & *Herba* | between about 2 mgms and 12 mgms, with the preferred amount being 7 mgms. |
| Total Weight in the preferred embodiment | 25 mgms. |

The ground herbal mixture is made of a mixture of the herbs which are ground using common means to form a finely particulate mixture, having the consistency of flour. The herbal oil mixture is made of extracted oils which are then mixed in the above described amounts to form the herbal oil mixture. The herbal oil mixture and the ground herbal mixtures are then added together, to form a paste-like material. The paste material is then formed within a gel capsule, which may then be dispensed.

In use, the mixture gel capsule herein described is taken three times a day, for a duration of up to fifteen days. After fifteen days the user discontinues the use of the treatment for a period of ten days, and the user is, during this time, examined. During the examination, appropriate diagnostic tests are performed, including either blood or urine chemical analysis, to evaluate the user's response to the therapy. The dosage, or daily regimen, may be then adjusted upwards or downwards as determined by the test results.

The mixture herein described is thought to affect the amount of required insulin for insulin dependent diabetics. The mixture herein described enhances function and healing of the pancreas, aids in blood pressure control and regulation, aids in the regulation and control of Cholesterol levels, and improves vision.

In another embodiment, the mixture may be ingested as a mixture within a liquid, such as a tea or drink. This modality of administration may be preferable for those persons who have difficulty swallowing capsules, or who would prefer a readily drinkable treatment.

In another embodiment, the mixture may be ingested as a mixture with a solid food, or soft food, such as oatmeal or pureed fruit. For use in the embodiment which do not require a gel capsule, the mixture may be dispensed as a paste in a jar, and the paste may then be mixed with a liquid for drinking, or a soft food for eating. Included in this embodiment is the use of a filler, or carrier, to give bulk to the mixture of the oil and ground herbs. Such a carrier may be any commercially available agent, which is well known in the art, and not herein discussed.

Like medications, specific herbs have specific pharmacologic properties, and the use of specific herbs has specific beneficial objectives.

The herbal oils selected have boiling points that are higher than are encountered in normal ambient temperatures, and therefore will not readily vaporize.

As to the manner of usage and operation of the present invention, the same should be apparent from the above description. Accordingly, no further discussion relating to the manner of usage and operation will be provided.

With respect to the above description then, it is to be realized that the optimum relationships for the components of the invention, are deemed readily apparent and obvious to one skilled in the art, and all equivalent relationships described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact formulation as described, and accordingly, all suitable modifications and equivalents may be resorted to, falling within the scope of the invention.

What is claimed as being new and desired to be protected by Letters Patent of the United States is as follows:

1. An herbal composition for Diabetes mellitus, Type II comprising: a mixture of herbal oils having a first volume; and a mixture of ground herbs having a first weight; the first volume and the first weight being mixed together; the first volume comprising: 30 drops of *Juniperum communis,* 30 drops of *Eucalyptus globulus,* 38 drops of *Rosmarinus officinalis*, and 38 drops of *Citrus medica* var. *Limonum*; the first weight comprising: 5 mgs of *Galega officinalis herba,* 7 mgs of *Myrtilli fructus* (bacca) *herba,* 6 mgs of *Carataegus fructus herba*, and 7 mgs of *Cynosbati fructus sine semimibus & herba.*

2. The herbal composition as described in claim 1, wherein said herbal composition is contained in a gel capsule.

3. The herbal composition of claim 1 in the form of a paste.

4. An herbal composition for Diabetes mellitus, Type II comprising: a first volume comprising: between about 20 and 40 drops of *Juniperum communis*, between about 20 and 40 drops of *Eucalyptus globulus*, between about 20 and 60 drops of *Rosmarinus officinalis*, and between about 20 and 60 drops of *Citrus medica* var. *Limonum*; and a first weight comprising: between about 1 and 10 mgs of *Galega officinalis herba*, between about 2 and 12 mgs of *Myrtilli fructus* (bacca) *herba*, between about 2 and 10 mgs of *Carataegus fructus herba*, and between about 2 and 12 mgs of *Cynosbati fructus sine semimibus & herba.*

\* \* \* \* \*